United States Patent [19]
Salvati

[11] Patent Number: 4,998,166
[45] Date of Patent: Mar. 5, 1991

[54] AUXILIARY LIGHT APPARATUS FOR BORESCOPE

[75] Inventor: Jon Salvati, Skaneateles, N.Y.

[73] Assignee: Welch Allyn, Inc., Skaneateles Falls, N.Y.

[21] Appl. No.: 452,107

[22] Filed: Dec. 18, 1989

[51] Int. Cl.⁵ .......................... H04N 7/18; A61B 1/06
[52] U.S. Cl. .................................. 358/100; 358/98; 128/6
[58] Field of Search ................. 358/98, 93, 100, 210, 358/229, 901; 128/4, 6

[56] References Cited

U.S. PATENT DOCUMENTS

| | | | |
|---|---|---|---|
| 4,475,539 | 10/1984 | Konomura | 358/98 |
| 4,491,365 | 1/1985 | Danna et al. | 358/98 |
| 4,523,224 | 6/1985 | Longacre et al. | 358/42 |
| 4,539,586 | 9/1985 | Danna et al. | 358/98 |
| 4,546,379 | 10/1985 | Sarofien et al. | 358/42 |
| 4,601,284 | 7/1986 | Arakawa et al. | 358/98 |
| 4,621,618 | 11/1986 | Omagiri | 358/98 |
| 4,755,873 | 7/1988 | Kobayashi | 358/98 |
| 4,862,253 | 8/1989 | English et al. | 358/42 |

Primary Examiner—John K. Peng
Attorney, Agent, or Firm—Wall and Roehrig

[57] ABSTRACT

An auxiliary light apparatus for a color video borescope has an auxiliary box that is connected by an umbilical to a receptacle on the video processor unit for the borescope. The insertion tube of the borescope has an interface module which normally connects to a receptacle in the video processor, but also fits a receptacle in the auxiliary box. Sequential primary color illumination is generated in the auxiliary box and supplied through the interface module and a fiber optic bundle in the insertion tube to the distal end of the tube to illuminate a remote target area. The auxiliary sequential light generator is optically synchronized from the main light generator within the video processor.

5 Claims, 3 Drawing Sheets 4,998,166

AUXILIARY LIGHT APPARATUS FOR BORESCOPE

BACKGROUND OF THE INVENTION

This invention relates to endoscopes or borescopes of the type in which a miniature video camera is mounted at the distal end of a flexible elongated insertion tube, and in which illumination is carried on a fiber optic bundle to the distal end of the insertion tube to illuminate a remote target area.

The invention is more particularly concerned with apparatus to extend the range of the borescope or endoscope, that is, devices which increase the separation from the target area to the associated video processor unit.

Currently, video borescopes are limited in length to about fifty feet (sixteen meters). This distance represents the maximum effective distance that the fiber optic bundle in the insertion tube can carry illumination for illuminating the target area. As a result, it is sometimes necessary to place the video processor in a precarious or highly inconvenient location just to permit the borescope to reach a desired remote target area, which may be deep within a turbine, boiler, or other complex piece of equipment.

Where a color endoscope or borescope is employed, sequential primary color light is supplied over the fiber optic bundle to illuminate the target area sequentially with red, blue, and green light. This can be generated using a white light source and separated into primary colors with a color filter wheel, whose rotation speed and phase are synchronized with the field rate of the video signal produced by the video camera. A sequential color light wheel device of this type is disclosed in Longacre U.S. Pat. No. 4,523,224. This device is conventionally contained within the video processor unit of the endoscope or borescope system.

An interface module at the proximal end of the borescope insertion tube, or at the proximal end of an umbilical or extension coupled to the insertion tube, removably couples to the video processor unit. This interface module includes electrical connectors to connect the video camera to circuitry in the video processor. The interface module also includes an optical interface that couples the proximal end of the fiber optic bundle to the sequential color light source within the video processor unit. An interface module of this type is disclosed in Danna et al. U.S. Pat. No. 4,539,586.

An auxiliary light device for a color borescope is described in U.S. Pat. No. 4,853,774, issued Aug. 1, 1989, and having a common assignee. This device is disposed between the probe interface module and the receptacle of the video processor. Sequential primary light is generated in the device and this is synchronized by special electrical conductors that connect to the video processor. A special modification to the processor is required for this.

OBJECTS AND SUMMARY OF THE INVENTION

It is an object of this invention to provide apparatus that extends the range of a borescope or endoscope without degradation of illumination, and without affecting the video signal produced by the video camera or imager in the device.

It is another object of the invention to provide apparatus which can be inserted between the endoscope or borescope's interface module and the socket or receptacle therefor in the video processor.

It is yet another object of the invention to extend the borescope or endoscope range without modification to the existing video processor.

According to an aspect of the invention, auxiliary illumination apparatus for a borescope to extend its range or working distance comprises a housing, a receptacle in the housing to receive the borescope interface module, a multiple contact connector mounted on the housing, and an electrical wiring harness within the housing with connectors to connect the pins or contacts of the interface module with corresponding pins of the multiple contact connector. An illumination source is situated within the housing with an optical interface disposed at the receptacle for supplying suitable illumination through the fiber optic bundle to the target area at the distal end of the borescope insertion tube. Preferably, this illumination source includes a color filter wheel and suitable control electronics within the housing. A flexible liquid light conduit, or the like, brings the light from the external source to the color wheel. The illumination fed to the fiber optic bundle is a sequence of primary colors which are synchronized with the fields of the video signal.

An umbilical connects this auxiliary apparatus to the video processor unit, and permits the auxiliary apparatus to be remoted from it a sufficient distance. The umbilical includes a sheath that carries a number of conductors, and a distal end connector which contacts these conductors with respective pins or contacts of the multiple contact connector. At the proximal end of the umbilical is an auxiliary interface module that mates with the receptacle in the video processor unit. This connects the appropriate conductors to send power, synchronizing signals and auxiliary signals to the video camera in the borescope, and to receive the video signals from it. To bring the appropriate power and synchronizing signals to the color filter wheel circuitry, a sensor (i.e., a red-sensitive photodetector) receives the output of the main color filter wheel of the video processor. The output of this detector is carried on a conductor in the umbilical and the color filter wheel of the auxiliary illumination apparatus locks in phase with the lamp and main color filter wheel in the video processor. The video and electrical signals are passed straight through the umbilical and apparatus, but the sequential primary color light is generated in the auxiliary apparatus. A slave circuit that employs a phase-lock loop can be employed for this purpose.

The above and many other objects, features, and advantages of this invention will become more fully understood from the ensuing description of a preferred embodiment which should be read in connection with the accompanying Drawing.

DETAILED DESCRIPTION OF A PREFERRED EMBODIMENT

Figure 1:
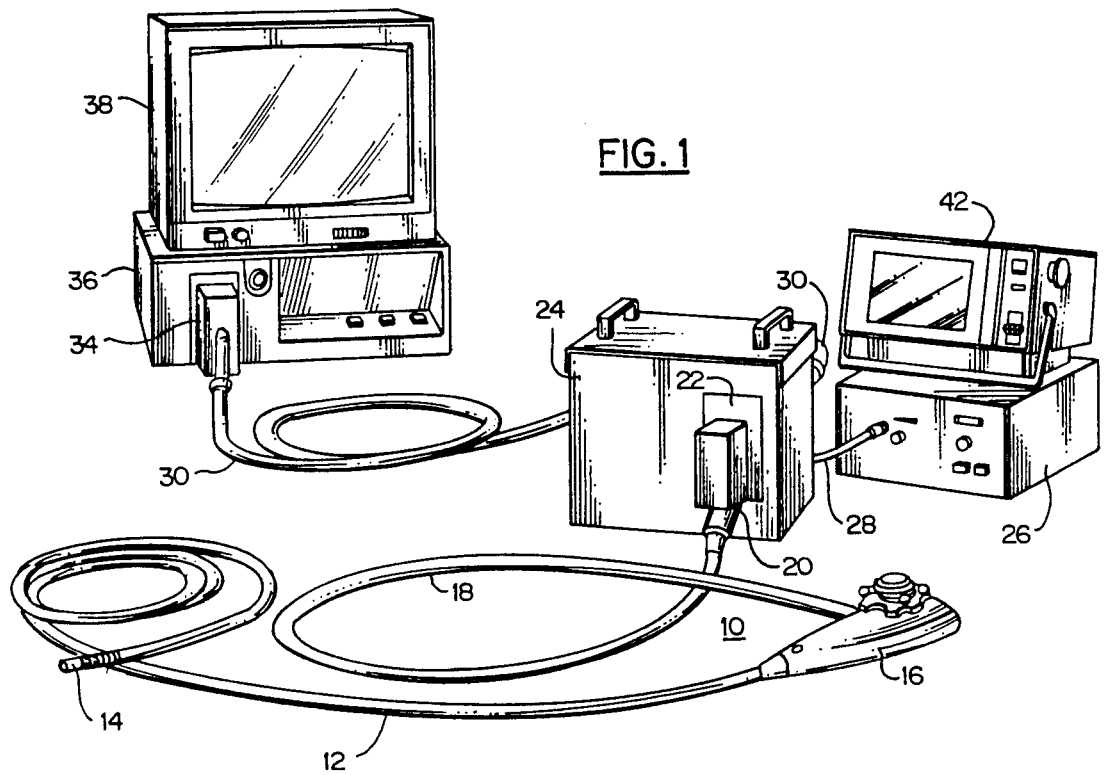
FIG. 1 is a perspective assembly view of a borescope with auxiliary illuminating apparatus according to one embodiment of this invention.

With reference to the Drawing, FIG. 1 shows a video borescope assembly which comprises a borescope 10 having an elongated, flexible insertion tube 12 approximately fifty feet (sixteen meters) in length. A viewing head 14 is incorporated into the distal end of the tube 12. This viewing head contains optical lenses and a miniature camera. The camera can be a CCD device or other solid state imager capable of providing a full-color image of a remote target area, e.g. the inside of a boiler tube of a heat exchanger, or a stator vane of a turbine. An example of a suitable solid state imager is disclosed in U.S. Pat. No. 4,491,865.

At the proximal end of the insertion tube 12 is a steering and control unit 16 which couples the insertion tube 12 to a flexible tubular umbilical or extension 18. At the proximal end of the umbilical 18 is a borescope interface module 20 of the plug-in type, substantially as disclosed in U.S. Pat. No. 4,539,586. The module 20 fits a mating receptacle 22 in an auxiliary light box 24. This light box is coupled in turn to an auxiliary illumination source 26 by means of a suitable flexible light guide 28. In this case the light guide 28 is a liquid light guide. An auxiliary umbilical 30, which is a flexible sheath containing a plurality of conductors, extends from a rear side 32 of the auxiliary light box 24 and has an auxiliary interface module 34 that fits a receptacle on a video processor unit 36.

The auxiliary interface module 34 is structurally and functionally similar to the borescope interface module 20, and serves to connect corresponding conductors in the borescope insertion tube 12 to the video processor unit 36. This feed-through provides video signals to a video monitor or screen 38 to produce an image of the remote target area.

As shown in FIG. 1, an auxiliary video monitor can be remoted to the location of the auxiliary light box, if desired.

The borescope insertion tube 12 has a wire bundle within it to carry video signals, synchronizing signals, power and auxiliary signals between the video processor unit 36 and the imager of the viewing head 14. Also, there is a fiber optic bundle extending through the insertion tube 12 and umbilical 18 to carry illumination from a main sequential primary color generator in the video processor unit 36 to the distal tip of the borescope insertion tube 12 to illuminate the target area. Because of intrinsic characteristics of this fiber optic bundle, the insertion tube is limited to a maximum length of fifty feet. Beyond that distance, transmission losses in the bundle prevent sufficient illumination to obtain a clear color video signal.

The interfacing of the fiber optic bundle to the color illumination generator is carried out by the interface module 20, such as the one as explained in U.S. Pat. No. 4,539,586.

Inspection of equipment with this type of borescope becomes difficult for confined areas, such as a boiler manifold, where there is insufficient space for the video processor unit. In such case, the auxiliary light unit 26 can be employed to remote the video processor unit by several meters.

Figure 2:
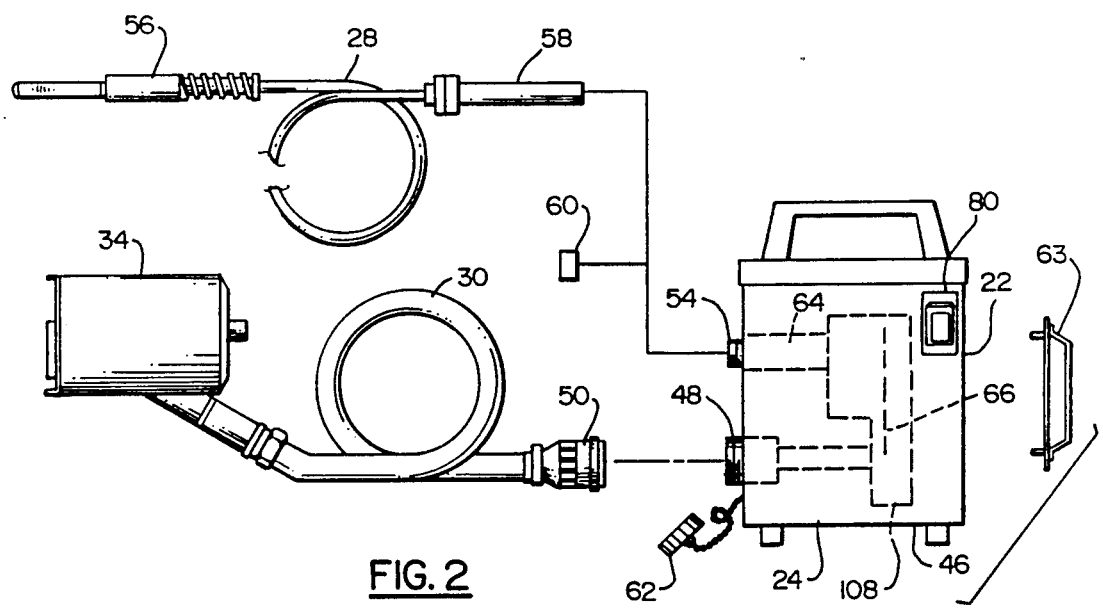
FIG. 2 is a partly exploded side view of the apparatus of this embodiment.

As shown in FIG. 2, the auxiliary light box 24 is formed of a housing or case 46 with a multiple-pin connector 48 mounted on its rear wall 32. This connects with a mating multiple contact connector 50 on the distal end of the auxiliary umbilical 30.

A receptacle 54 for the light conduit 28 is also located on the rear wall 32 of the auxiliary box 24.

The light guide or conduit 28 has a male fitting 56 at its proximal end to connect to a suitable fitting at the auxiliary lamp unit 26. An adapter can be employed to mate this fitting to other light sources. At the distal end of the light guide 28 is a male coupling or probe 58 which is inserted into the receptacle 54 on the auxiliary box 24, protruding to a position adjacent the receptacle 22. A retaining nut 60 with inside threads retains the probe 58 in the receptacle 54. A dust cap 62 is provided for the multiple pin connector 48 and a dust cover 63 is provided for the receptacle 22.

Figure 3:
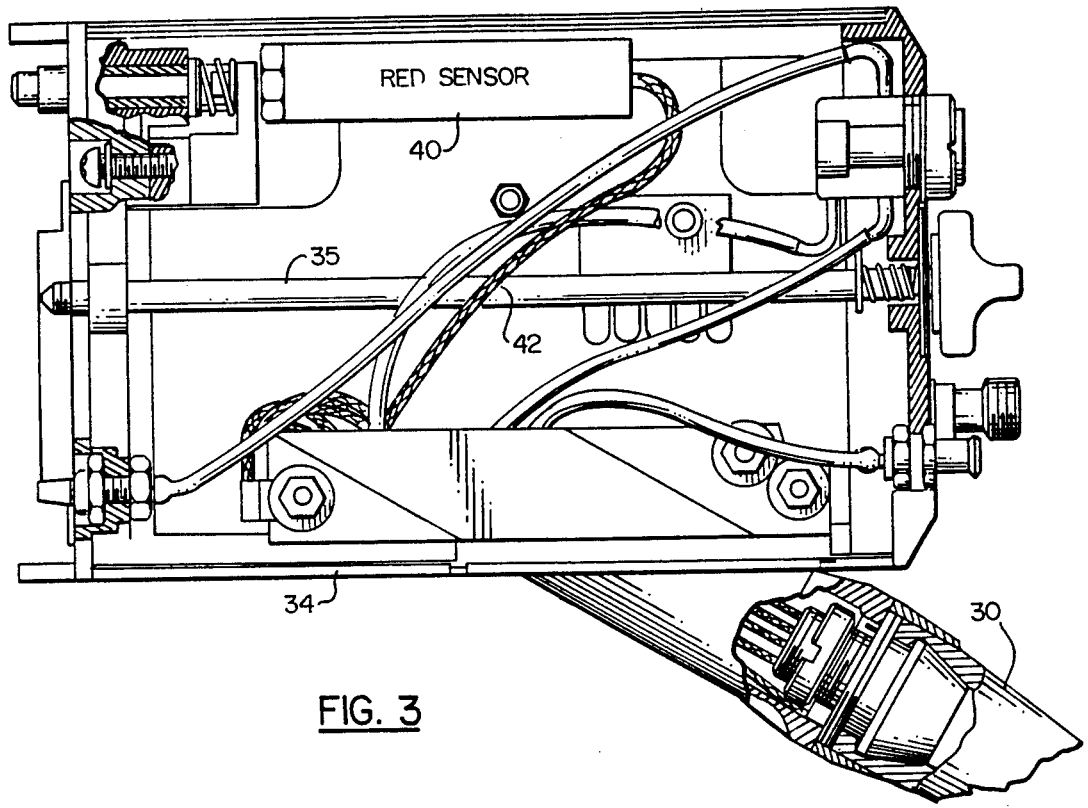
FIG. 3 is a sectional elevation of an auxiliary interface module of this embodiment.

As shown in FIG. 3, the auxiliary interface module 34 is basically similar to the module of U.S. Pat. No. 4,539,586, with a screw rod 35 that extends longitudinally through the module and engaging a threaded bore within the receptacle of the processor 36. There are also numerous electrical connections made between conductors of the umbilical 30 and the processor 36. Unlike the module 20 of the borescope assembly, and unlike the interface module disclosed in U.S. Pat. No. 4,539,586, a red light sensor 40 is included in the module 34 in place of the usual light transmitting fiber optic bundle. This sensor 40 can be a barcode reader wand. This sensor provides a pulse signal over a conductor to the auxiliary light box 24 through the umbilical 30.

Figure 4:
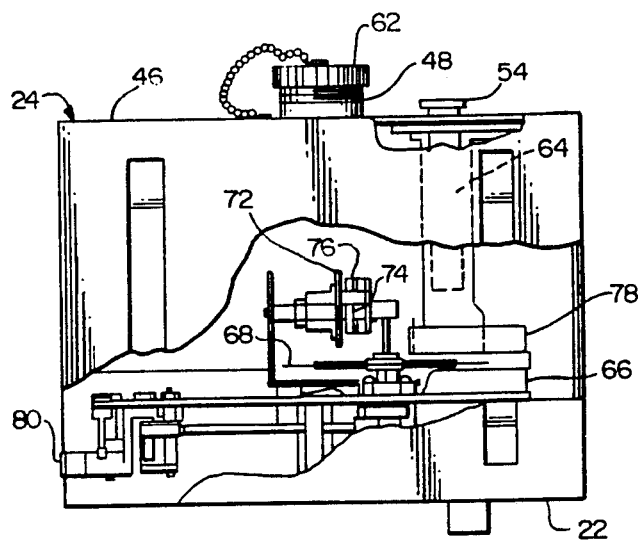
FIG. 4 is a top plan view of the apparatus with a portion of the housing removed.

As further shown in FIG. 4, the housing 46 of the auxiliary box 24 has a sleeve 64 within it connected to the receptacle 54 to guide the light guide probe 58 to a suitable position with respect to a color generator 66, which can be of the same general construction as disclosed in U.S. Pat. No. 4,523,224. This generator includes a rotary color filter wheel 68 which presents a succession of red, blue, and green filters between the end of the probe 58 and the receptacle 22. A synchronous motor or stepper motor 70 drives the color filter wheel 68 in synchronism with the color wheel of the processor 36, employing the color pulse signal from the sensor 40. Synchronizing signals are generated in the video processor units including a lamp-enable signal LEN generated at the field rate and a sweep signal $\phi p$ that corresponds to twice the line or horizontal sweep rate. The box 24 can be used for either NTSC or PAL systems, as preferred, depending on how the signals $\phi p$ and LEN are handled.

As shown in FIG. 4, the auxiliary color generator includes a motor driver circuit printed circuit board 72. A timing pin 74 on the shaft of the motor 70 passes a magnetic or optical sensor 76 which produces a pulse when the motor shaft reaches a predetermined angular position. The color generator also includes suitable interface optics 78, and a color/monochrome selector which can constructed as described in U.S. Pat. No. 4,862,253, having a common assignee herewith.

Figure 5:
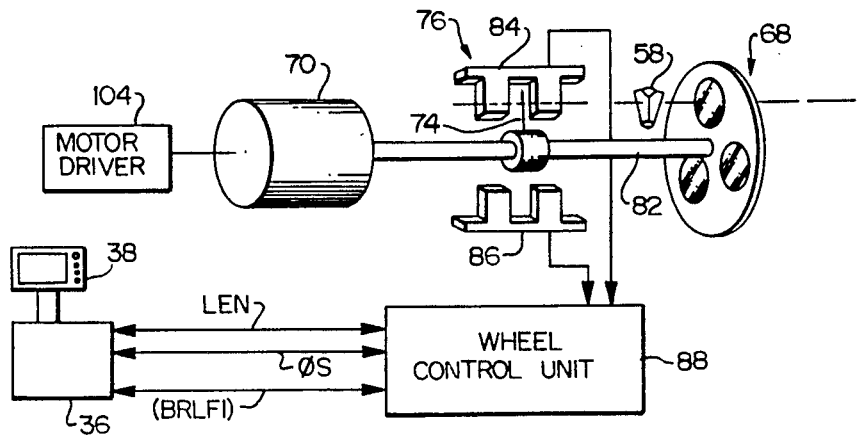
FIG. 5 is a schematic view of the color filter wheel of the apparatus of this embodiment.

As shown in more detail in FIG. 5 the timing pin 74 is mounted on a shaft 82 of the motor 70 to rotate with the color wheel 68. The rotary position sensor 76 here includes a first optical sensor 84 and a second optical sensor 86 angularly spaced by a predetermined angle. These sensors provide position or index pulses $I_1$ and $I_2$ that are phase separated from one another by the same predetermined angle.

On the motor driver circuit board 72 a wheel control unit 88 sends motor drive control signals $\phi_1$, $\phi_2$, $\phi_3$ and $\phi_4$ in response to the position pulses $I_1$, $I_2$ from the sensors 84 and 86, in response to timing pulses s that corresponds to the horizontal synch pulses, and in response to a blue-red field index signal BRLFI. This signal BRLFI is generated in response to color pulses from the sensor 40 and in response to the lamp enable signal LEN, which is sent to the video camera at the field rate from the processor unit.

Within the enclosure 46 of the auxiliary box 24 is a wiring harness, not specifically shown, but which has a plurality of conductors which connect the receptacle 22 directly to the multiple pin connector 48, for connection via the connector 50, auxiliary umbilical 30 and auxiliary interface module 34, to the video processor unit 36. Some of those conductors in the wiring harness connect between the video processor 36 and the video camera, and these can be used to power and synchronize the motor 70 of the color signal generator. In particular, these conductors carry power at +5 volts, +12 volts, and −12 volts, and also carry the signal LEN provided at the video field rate and the signal $\phi p$ provided at twice the line rate.

The apparatus of this embodiment provides straight passthrough of electrical signals between the borescope imager and the video processor unit 36. However, the color sequential illumination is generated in the auxiliary box 24 at a distance from the unit 36. This permits the monitor 38 and video processor unit 36 to be remoted at a desired location away from the target area without exceeding the critical limit mentioned earlier.

No modification is required to the video processor unit, or its internal wiring.

Figure 6:
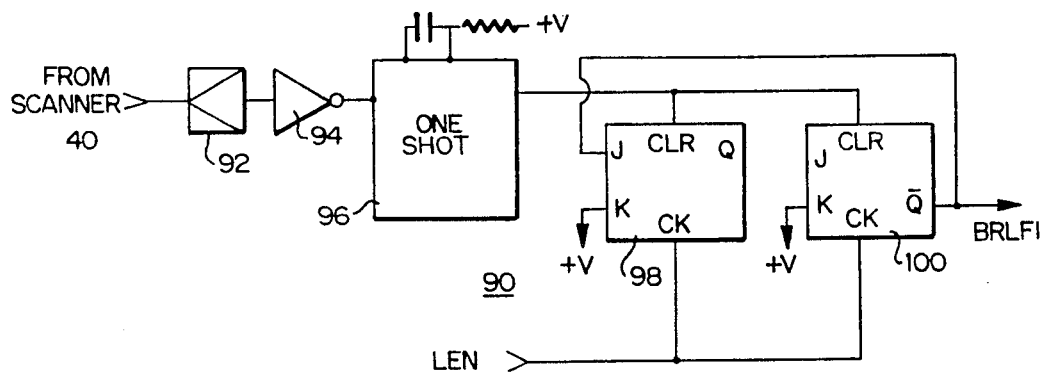
FIG. 6 is a schematic circuit diagram of synchronization and control circuit of this embodiment.
Figure 7:
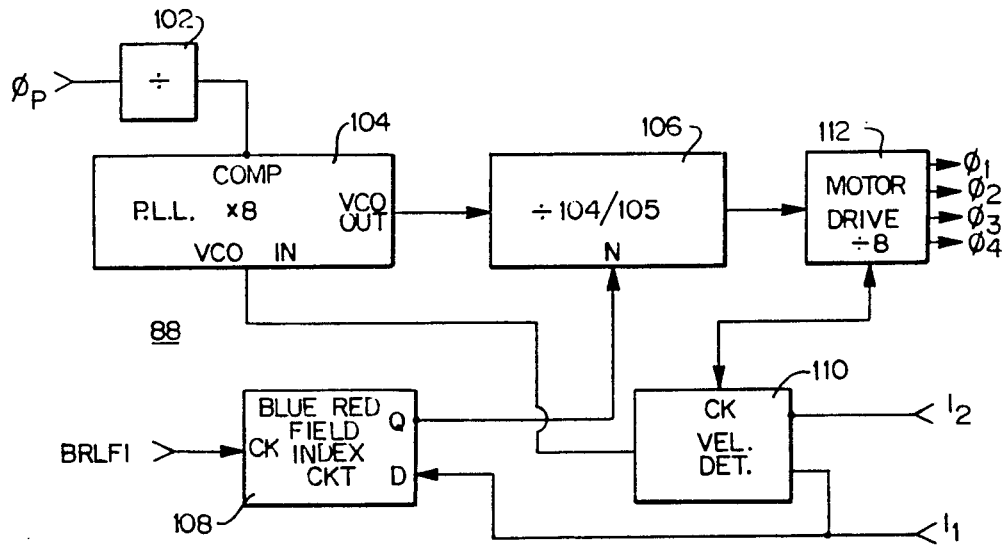
FIG. 7 is a schematic circuit diagram of a field index circuit of this embodiment.

The color wheel synchronization circuitry can by constructed as generally shown in FIGS. 6 and 7.

FIG. 6 shows a divide-by-three circuit 90 to generate a blue-red field index signal BRLFI synchronized with the red color pulses from the scanner or sensor 40. Here, the red color pulses are fed through an amplifier 92 and inverter 94 to a one-shot multivibrator 96 that shapes the pulse train, e.g., serving as a blue-to-red transition detector. The output of this one-shot is fed to clear terminals of a pair of JK flip flops 98 and 100 that are connected to serve as a divide-by-three counter. These flip flops 98, 100 are clocked by the light enable signal LEN that is furnished on the conductors passing through the auxiliary light box wiring harness. The output of the circuit 90 is the signal BRLFI provided us at pulses one-third the field rate and timed to coincide with the transition from the blue to the red filter on the main color wheel in the processor unit 36.

As shown in FIG. 7 the wheel control circuit 88 has a frequency divider 102 that receives the signal $\phi P$ and feeds a divided-down pulse train to a phase-locked loop circuit 104. This circuit 104 generates an output frequency that is fed to another frequency divider 106 whose divisor can be controlled e.g. between "104" and "105" for NTSC or between "124" and "125" for PAL, by a control signal from an index circuit 108. The index signal BRLFI is fed to a clock input of the circuit 108 while the index pulse $I_1$ from the optical sensor 84 is applied to a D terminal thereof, so that the output signal from the Q terminal of this circuit 104 depends on the relative timing of the index signals BRLFI and $I_1$. A velocity detector circuit 110 is a logic circuit which is input with the position index pulses $I_1$ and $I_2$ and produces an error signal that is fed to a VCO input terminal of the phase locked loop circuit. The output of the divider 106 is fed to a motor drive circuit 112 which further divides the frequency by 8 and provides four phase drive signal $\phi_1$, $\phi_2$, $\phi_3$, and $\phi_4$, to the motor and also provides a field-rate clock signal to the velocity defector circuit 110. Details of this circuit can be seen in U.S. Pat. No. 4,523,224. The exact circuitry used can be varied to obtain the same results.

When there is a wide discrepancy in phase or motor velocity between the main and auxiliary color light generators, the velocity detector 110 will adjust the error signal fed to the phase-locked loop circuit 104. However for minor phase adjustment, the index circuit 108 will adjust the divisor of the frequency divider 106 to correct the phase of the motor drive signals $\phi_1$ to $\phi_4$.

Although in this embodiment the sensor 40 is sensitive to red light, in other embodiments a green - or blue-sensitive device could be employed, either within the interface module 34, as illustrated, or within the auxiliary box and coupled by fiber optics to the main color generator in the processor 36.

It should be appreciated that this device permits extension from existing, unmodified video processors, so that the same auxiliary box 24 could be employed with a variety of borescope or endoscope systems.

Also, while this invention has been employed with a borescope in this example, the same or similar system could be employed with a medical or veterinary endoscope, if desired.

Here, this invention has been described with reference to one particular embodiment, but it should be recognized the invention is not limited to that embodiment. Rather, many modifications and variations would present themselves to those of skill in the art without departing from the scope and spirit of this invention, as defined in the appended claims.

What is claimed is:

1. Auxiliary illumination apparatus for extending the working distance between a remote target area and a video processor unit for a video borescope or endoscope of the type which includes an elongated flexible insertion tube, an interface module coupled to a mating receptacle coupler in said video processor unit for supplying power, synchronizing signals, and auxiliary signals from said video processor device and to receive and process video signals produced by said video camera, and further including an optical interface for coupling an illumination source in said video processor unit to a proximal end of a fiber optic bundle within said insertion tube which carries illumination to the distal end of said insertion tube to illuminate said target area, wherein the illumination source in said video processor generates sequential primary color illumination at a video field rate; the auxiliary apparatus comprising
   a housing;
   receptacle means in said housing for receiving said interface module;
   a multiple contact connector mounted on the housing;
   electrical harness means within the housing that includes a plurality of conductors that terminate at said receptacle means and at said multiple contact connector;
   a sequential primary color illumination generator within said housing, including an optical interface disposed at said receptacle means for supplying sequential primary color illumination through said fiber optic bundle to the target area;

an umbilical that includes a flexible elongated sheath, a plurality of conductors within said sheath, a distal end connector to couple said plurality of conductors to said electrical harness means, an auxiliary interface module at a proximal end of said umbilical which mates with mating receptacle coupler in said video processor unit and connected to said conductors in said umbilical for providing power, synchronizing signals, and auxiliary signals over said conductors and through said electrical harness and said insertion tube to said camera and to carry the video signals from said camera to the video processor unit, and a color detector in said auxiliary interface module facing the illumination source in said video processor providing color identification pulses along a conductor in said umbilical to correspond to occurrences of light of a predetermined one of said primary colors; and synchronizing means in said housing for synchronizing the sequential primary color illumination generator in said housing with the sequential primary color illumination generated by the illumination source in said video processor based on the color pulses from said color detector and synchronizing signals carried through said umbilical and wiring harness to said insertion tube.

2. An auxiliary illumination apparatus according to claim 1 wherein said synchronizing means includes a divide-by-three counter having a clocking input to which is supplied a synchronizing signal carried on a conductor in said umbilical and wiring harness and which occurs at the video field rate, reset means that is supplied with said color identification pulses, and an output providing a primary-color field index signal.

3. An auxiliary illumination apparatus according to claim 2 wherein said reset means includes a pulse shaper circuit supplied with said color pulses and having an output coupled to a clear terminal of said divide-by-three counter.

4. An auxiliary illumination apparatus according to claim 3 wherein said pulse shaper includes an inverter followed by a one-shot multivibrator.

5. An auxiliary illumination apparatus according to claim 1 wherein said primary color is red and said color detector includes red-sensitive bar-code scanner unit included in said auxiliary interface module.

* * * * *